(12) United States Patent
Zesch et al.

(10) Patent No.: US 7,879,598 B2
(45) Date of Patent: Feb. 1, 2011

(54) MULTIANALYTE DETERMINATION SYSTEM AND METHODS

(75) Inventors: Wolfgang Zesch, Zürich (CH); Martin Andreas Bopp, Basel (CH); Michael Pawlak, Laufenburg (DE)

(73) Assignee: Bayer Technology Services GmbH, Leverkusen (DE)

( * ) Notice: Subject to any disclaimer, the term of this patent is extended or adjusted under 35 U.S.C. 154(b) by 2160 days.

(21) Appl. No.: 10/363,577

(22) PCT Filed: Aug. 30, 2001

(86) PCT No.: PCT/EP01/10012

§ 371 (c)(1), (2), (4) Date: Mar. 4, 2003

(87) PCT Pub. No.: WO02/21110

PCT Pub. Date: Mar. 14, 2002

(65) Prior Publication Data

US 2004/0038386 A1 Feb. 26, 2004

(30) Foreign Application Priority Data

Sep. 4, 2000 (CH) .................................... 1718/00

(51) Int. Cl.
*C12M 1/34* (2006.01)
(52) U.S. Cl. .................... 435/288.7; 356/36; 356/38; 356/305; 435/283.1; 436/164; 436/166
(58) Field of Classification Search .......... None
See application file for complete search history.

(56) References Cited

U.S. PATENT DOCUMENTS 3,839,634 A * 10/1974 Buchmann ............ 250/214 VT
4,698,734 A 10/1987 Ngai
4,847,479 A * 7/1989 Clark et al. ............... 250/201.1
4,877,747 A * 10/1989 Stewart ...................... 436/525
5,071,248 A 12/1991 Tiefenthaler et al.
5,143,854 A * 9/1992 Pirrung et al. .............. 436/518
5,192,506 A * 3/1993 Kureshy et al. ............... 422/64

(Continued)

FOREIGN PATENT DOCUMENTS

DE 40 11 730 10/1990

(Continued)

OTHER PUBLICATIONS

Boyd et al., Bending losses of dielectric slab optical waveguide with double or multiple claddings; Jul. 1976, App Optics 15(7): pp. 1681-164.*

*Primary Examiner*—Nelson C. Yang
(74) *Attorney, Agent, or Firm*—Wenderoth, Lind & Ponack, L.L.P.

(57) ABSTRACT

The invention relates to embodiments of an optical system for luminescence determination, comprising two or more excitation light sources, a sensor platform and an optical component with several discrete facets for beam deflection towards the sensor platform. Further subjects of the invention are methods for luminescence determination with an optical system according to the invention and analytical systems, as well as the use of these methods for quantitative affinity sensing and for various other applications. The aim of the present invention is to provide optical and analytical measuring devices for highly sensitive detection of one or more analytes, using a multitude of measurement areas on a common carrier.

103 Claims, 2 Drawing Sheets

U.S. PATENT DOCUMENTS

| | | | |
|---|---|---|---|
| 5,445,934 A | 8/1995 | Fodor et al. | |
| 5,631,734 A | 5/1997 | Stern et al. | |
| 5,822,472 A | 10/1998 | Danielzik et al. | |
| 5,959,292 A | 9/1999 | Duveneck et al. | |
| 5,982,534 A * | 11/1999 | Pinkel et al. | 359/387 |
| 6,044,196 A | 3/2000 | Winston et al. | |
| 6,078,705 A | 6/2000 | Neuschafer et al. | |
| 6,178,224 B1 * | 1/2001 | Polichar et al. | 378/98.2 |
| 6,493,090 B1 * | 12/2002 | Lading et al. | 356/484 |
| 6,499,366 B1 * | 12/2002 | Meadows et al. | 73/864.81 |
| 2002/0076154 A1 * | 6/2002 | Maisenhoelder et al. | 385/37 |

FOREIGN PATENT DOCUMENTS

| | | |
|---|---|---|
| DE | 196 28 002 | 12/1997 |
| WO | 94/27137 | 11/1994 |
| WO | 95/33197 | 12/1995 |
| WO | 95/33198 | 12/1995 |
| WO | 96/35940 | 11/1996 |
| WO | 97/35203 | 9/1997 |
| WO | 97/37211 | 10/1997 |
| WO | 98/08077 | 2/1998 |
| WO | 98/58963 | 12/1998 |
| WO | 00/75644 | 12/2000 |
| WO | 01/13096 | 2/2001 |

* cited by examiner

MULTIANALYTE DETERMINATION SYSTEM AND METHODS

This application is a national stage entry of PCT/EP01/10012, filed Aug. 30, 2001.

The invention relates to embodiments of an optical system for luminescence determination, comprising two or more excitation light sources, a sensor platform and an optical component with several discrete facets for beam deflection towards the sensor platform. Further subjects of the invention are methods for luminescence determination based thereon, with an optical system according to the invention, and analytical systems, as well as the use of these methods for quantitative affinity sensing and for various other applications.

The aim of the present invention is to provide optical and analytical measuring devices for highly sensitive detection of one or more analytes, using a multitude of measurement areas on a common carrier.

Under the attribute "biochips" various measurement devices for multianalyte detection have become known during the last years, wherein a multitude of different biological or biochemical recognition elements is immobilized on a carrier, such as a glass plate or a microscope slide, to which recognition elements different analytes are bound in the course of the determination method. Most often the detection is performed using optical methods, for example upon detection of luminescence or more specifically fluorescence from so-called luminescence or fluorescence labels that are applied during the assay. The discrete measurement areas with different recognition elements are generally called "features".

For example in U.S. Pat. No. 5,445,934 (Affymax Technologies) arrays of oligonucleotides with a density of more than 1000 features per square centimeter are described and claimed. The excitation and read-out of such arrays is based on classical optical methods (epi-fluorescence excitation and detection, i.e. direct excitation of the features or measurement areas in an configuration of direct irradiation, see below). The whole array can be illuminated using an expanded excitation light bundle, which, however, results in relatively low sensitivity, as the fraction of scattered light is relatively large and as scattered light or background fluorescence light from the glass substrate (carrier) is generated also in those regions where no immobilized oligonucleotides for analyte binding are located. In order to limit the excitation and detection to the regions of the immobilized features and to discriminate light generation in the adjacent areas, confocal microscopic measurement configurations are often used, and the different features are read out sequentially by "scanners", i.e. upon sequential excitation and luminescence detection by means of lateral translation of the excitation light focus on the glass plate using movable mirrors, or by means of lateral translation of the glass plate with respect to the excitation light beam. Such a scanner is, for example, described and claimed in U.S. Pat. No. 5,631,734. However, the sequential excitation and detection of the measurement areas results in a relatively long time needed for the read-out of an array with a large number of features. Additionally, the sensitivity of such classical excitation and detection configurations with direct illumination of the measurement areas, associated with the simultaneous illumination of a liquid volume that might be provided above said measurement areas, is not sufficient for many applications.

Typical values between 0.1 and 1 flurophore per $\mu m^2$ are reported as the detection limits defining the sensitivity of the best current scanners.

For achieving lower detection limits, measurement arrangements have been developed, wherein the determination of an analyte is based on its interaction with the evanescent field, which is associated with light guiding in an optical waveguide, wherein biochemical or biological recognition elements for the specific recognition and binding of the analyte molecules are immobilized on the surface of the waveguide.

When a light wave is coupled into an optical waveguide surrounded by optically rarer media, i.e. media of lower refractive index, the light wave is guided by total reflection at the interfaces of the waveguiding layer. In that arrangement, a fraction of the electromagnetic energy penetrates the media of lower refractive index. This portion is termed the evanescent (=decaying) field. The strength of the evanescent field depends to a very great extent on the thickness of the waveguiding layer itself and on the ratio of the refractive indices of the waveguiding layer and of the media surrounding it. In the case of thin waveguides, i.e. layer thicknesses that are the same as or smaller than the wavelength of the light to be guided, discrete modes of the guided light can be distinguished. As an advantage of such methods, the interaction with the analyte is limited to the penetration depth of the evanescent field into the adjacent medium, being of the order of some hundred nanometers, and interfering signals from the depth of the (bulk) medium can be mainly avoided. The first proposed measurement arrangements of this type were based on highly multi-modal, self-supporting single-layer waveguides, such as fibers or plates of transparent plastics or glass, with thicknesses from some hundred micrometers up to several millimeters.

In WO 94/27137, measurement arrangements are disclosed, wherein "patches" with different recognition elements, for the determination of different analytes, are immobilized on a self-supporting optical substrate waveguide (single-layer waveguide), excitation light being in-coupled at the distal surfaces ("front face" or "distal end" coupling), wherein laterally selective immobilization is performed using photo-activatable cross-linkers. According to the disclosure, several patches can be arranged row-wise in common, parallel flow channels or sample compartments, wherein the parallel flow channels or sample compartments extend over the whole length of the range on the waveguide used as a sensor, in order to avoid an impairment of light guiding in the waveguide. However, there are no hints to a two-dimensional integration of multiple patches and sample compartments. In a similar arrangement disclosed in WO 97/35203, several embodiments of an arrangement are described, wherein different recognition elements for the determination of different analytes are immobilized in separate, parallel flow channels or sample compartments for the sample and for calibration solutions of low and, optionally in addition, of high analyte concentration. Again, no hint is given to a possibility of two-dimensional arrangements.

For an improvement of the sensitivity and simultaneously for an easier manufacturing in mass production, planar thin-film waveguides have been proposed. In the simplest case, a planar thin-film waveguide consists of a three-layer system: support material (substrate), waveguiding layer, superstrate (respectively the sample to be analyzed), wherein the waveguiding layer has the highest refractive index. Additional intermediate layers can further improve the action of the planar waveguide.

Several methods for the in-coupling of excitation light into a planar waveguide are known. The methods used earliest were based on front face coupling or prism coupling, wherein generally a liquid is introduced between the prism and the waveguide, in order to reduce reflections due to air gaps. These two methods are mainly suited with respect to waveguides of relatively large layer thickness, i.e. especially self-supporting waveguides, and with respect to waveguides with a refractive index significantly below 2. For in-coupling of excitation light into very thin waveguiding layers of high refractive index, however, the use of coupling gratings is a significantly more elegant method. Thereby the coupling of the irradiated excitation light into the waveguiding layer, in which the grating is modulated, is effected when the coupling angle defined by the resonance condition for in-coupling is met. The actual in-coupling angle for excitation light of a certain wavelength is dependent on the refractive index of the waveguiding layer and that one of the adjacent media (carrier layer or substrate and "superstrate"), on the thickness of the waveguiding layer, on the diffraction order to be in-coupled (for efficient in-coupling typically the first diffraction order), and on the grating period. In case of very thin waveguiding films (of about 100 nm to 200 nm thickness with a refractive index >2), for the in-coupling of transversally electrically polarized light and of transversally magnetically polarized light each there is only one discrete coupling angle for in-coupling of the $TE_0$-mode or of the $TM_0$-mode, respectively. Such waveguides are called mono-modal (single-mode). The in-coupling angle changes with the excitation wavelength. For thin-film waveguides as they are described in more detail further below, comprising a waveguiding layer with refractive index of 2.2 and with about 150 nm layer thickness on a glass substrate (n=1.52; values for excitation light 0f 633 nm wavelength), the coupling angle changes by about 0.2° per 1 nm change of wavelength (for in-coupling angles between about +30° and −30° deviation from the direction perpendicular to the waveguide surface).

As a matter of experience, coupling angles in the range between +30° and −30° deviation from the direction perpendicular to the waveguide surface are preferred for efficient in-coupling, especially also in order to avoid the excitation of so-called substrate modes, i.e. of light-guiding not in the highly refractive waveguiding layer, but partially in the substrate located below, as the evanescent field to be used for analyte detection by luminescence detection is reduced in the presence of these substrate modes.

Besides on the parameters already mentioned, the sharpness of the resonance condition is dependent on the depth of the coupling grating. As a tendency, the resonance angle is defined much sharper (with a half-width of the order of 0.01° and below) for shallow gratings (for example with a grating depth of 5 nm-10 nm) than for deep gratings (with, for example, a grating depth of more than 25 nm). The diffraction efficiency of a grating, however, is the larger the deeper the grating is. From this diffraction efficiency, however, a correspondingly high coupling efficiency into the waveguiding film, with an unstructured region adjacent to the coupling grating, cannot be directly concluded, because not only the efficiency of in-coupling but also of immediate out-coupling does increase with increasing grating depth, the out-coupling occurring in the same direction as the reflection from the grating. Therefore, there is an optimum grating depth for the maximum in-coupling efficiency (under the described conditions in the range between 10 nm and 20 nm), which is also dependent on the geometry of the irradiated light beam (besides the dependence on the parameters already mentioned).

The described parameters are of high importance for the tolerances and for the required precision for the manufacturing of the optical and mechanical components of an adequate analytical system for luminescence excitation and detection applied to planar thin-film waveguides.

In this application, the term "luminescence" means the spontaneous emission of photons in the range from ultraviolet to infrared, after optical or other than optical excitation, such as electrical or chemical or biochemical or thermal excitation. For example, chemiluminescence, bioluminescence, electroluminescence, and especially fluorescence and phosphorescence are included under the term "luminescence".

By means of highly refractive thin-film waveguides, based on an only some hundred nanometers thin waveguiding film on a transparent support material, the sensitivity could be increased considerably during the last years. Detection limits between 0.01 and 0.001 fluorophores per $\mu m^2$ are achieved with such devices. In WO 95/33197, for example, a method is described, wherein the excitation light is coupled into the waveguiding film by a relief grating as a diffractive optical element. The luminescence that is excited in the evanescent field but isotropically emitted, from substances capable of luminescence that are located within the penetration depth of the evanescent field, is measured by adequate measurement arrangements, such as photodiodes, photomultipliers or CCD cameras. The portion of evanescently excited radiation, that has back-coupled into the waveguide, can also be out-coupled by a diffractive optical element, like a grating, and be measured. This method is described, for example, in WO 95/33198.

In order to perform, simultaneously or sequentially, exclusively luminescence-based, multiple measurements with essentially mono-modal, planar inorganic waveguides, for example in the specification WO 96/35940, arrangements (arrays) have been proposed, wherein at least two discrete waveguiding areas are provided on one sensor platform in such a way, that the excitation light guided in one waveguiding area is separated from other waveguiding areas.

In the spirit of this invention, spatially separated measurement areas (d) shall be defined by the closed area that is occupied by biological or biochemical or synthetic recognition elements immobilized thereon, for recognition of an analyte in a liquid sample. These areas can have any geometry, for example the form of dots, circles, rectangles, triangles, ellipses or lines.

The embodiments described by examples in the above referenced state-of-the-art of optical systems for fluorescence or luminescence excitation using sensor platforms based on planar waveguides are related, without any exception, to excitation using only a single excitation wavelength. In general, the described systems additionally require manual insertion of the sensor platform, followed by its careful adjustment with respect to the excitation and detection optics. In conclusion, these disclosed examples typically represent "home-made" constructions or prototypes, in the best case, which can be operated by a specialist, but not by a user with average education without profound special knowledge.

Therefore, there is a need for a system for the measurement of optical sensor platforms, that can be easily operated by a user and provides an automated adjustment, if possible.

Especially for applications in biology, for example for expression analysis, typically different fluorescence labels are used, which are excited at different wavelengths. As a response to this need, in case of commercially available scanning systems with excitation by direct illumination the excitation light from two or even more laser light sources can be directed onto the sample. Therefore, there is also a need for a system for the excitation of sensor platforms based on optical waveguides, which allows the application of at least two excitation wavelengths without requiring adjustments by the user.

The solution of this task is rendered difficult by various boundary conditions. For an efficient detection, i.e. collection of the isotropically emitted luminescence the application of imaging optics with a numerical aperture as high as possible, comparable to the optics of a microscope, is desired, leading to an only small working distance towards the sensor platform. Simultaneously, the area of the sensor platform shall be exploited as efficiently as possible, i.e. the unused local separation between the in-coupling gratings and the measurement areas shall be kept small, as the basic price of the sensor platform is dependent on the size of the area to a large extent. A very small separation between the in-coupling gratings and the measurement areas leads to geometrical difficulties to direct the excitation light towards the sensor platform, passing aside of the collection optics, and to avoid a shadowing of the field-of-view of the collection optics by beam-deflecting components, which may be located between the collection optics and the sensor platform. Finally, it has to be taken care of avoiding direct reflections of excitation light towards the collection optics and of avoiding a further propagation of such reflected light towards the detector.

The task is rendered still more difficult because it is desired for many applications to work with open sample compartments or open reception vessels, for receiving liquid exiting a sample compartment after the performance of washing steps or after sequential reagent application. Such a technical task requires an essentially horizontal positioning of the sensor platform, so that the adaptation of the adjustment to a change of the coupling angle due to a different excitation wavelength cannot be performed or can be performed to an only very limited extent by a rotation of the sensor platform with respect to the direction of the irradiated light.

The described tasks are solved by the invention disclosed in the following. Additionally, the optical system according to the invention is not only suited for luminescence excitation and detection on measurement areas on sensor platforms based on planar optical waveguides, but also of such platforms like glass plates, as they are used for conventional epi-illumination fluorescence excitation and detection.

Subject of the invention is an optical system for luminescence determination, comprising at least two excitation light sources, a sensor platform and an optical component with several discrete facets for deflecting a light beam, wherein the angle of divergence between excitation light falling onto different facets of said optical component is increased or reduced by at least a factor of 1.2 in the optical path departing from said optical component, in comparison to the original divergence angle (between said light rays irradiated onto said different facets).

As described above, the in-coupling angle for excitation light of different wavelength can differ significantly in case of highly refractive thin-film waveguides as sensor platforms, with diffractive gratings for the in-coupling of the excitation light and modulated in the high-refractive index layer. As an example, for sensor platforms comprising a 150 nm thin waveguiding layer of $Ta_2O_5$ (n=2.15 at 633 nm) on glass (n=1.52 at 633 nm) and about 12 nm deep gratings with a period of 318 nm, the in-coupling angle for excitation light of 492 nm is about +18° and of 670 nm about −17° (with air as the medium above the coupling grating).

For a compact construction of an optical system, however, it is in general hardly advantageous to direct the excitation light of different light sources from longer distances and from a plurality of different spatial directions onto a common target, instead of integrating different excitation light sources at a common location in a module. For example for embodiments of the optical system according to the invention, comprising thin-film waveguides as sensor platforms, it is therefore advantageous, if the angle of divergence between excitation light falling onto different facets of said optical component is increased by at least a factor of 1.2, preferably however by at least a factor of 1.5, in the optical path departing from said optical component, in comparison to the original divergence angle (between said light rays irradiated onto said different facets).

Said optical component with several discrete facets for beam deflection can be a multi-facet mirror with planar or curved facets, preferably with planar facets.

In another, preferred embodiment of the optical system according to the invention said optical component with several discrete facets for beam deflection is a multi-facet prism with planar or curved facets, preferably with planar facets.

In combination with different excitation light sources of similar or different wavelength a variety of different embodiments of the optical system are possible. One possible embodiment consists in that the light from two or more excitation light sources of similar or different wavelength falls onto the same facet of said optical component for beam deflection. Characteristic for another possible embodiment is, that a dedicated facet of said optical component is provided for each different excitation wavelength, the excitation light of said excitation wavelength to be directed onto the corresponding dedicated facet.

When changing between excitation light source of different wavelengths, the extent of necessary adjustments shall be kept as small as possible, in order to minimize, on one side, the time required for these adjustments, when the system is not available for acquisition of measurement data, and to minimize, on the other side, the travel ranges of the mechanical positioning components, which travel ranges have a direct impact on system costs. Therefore, it is preferred that the beam deflection of excitation light of different wavelength into different predefined directions occurs with an offset of less than 0.2 mm between the centers of the deflected beams on the sensor platform.

For achieving a high sensitivity in luminescence detection methods, it is generally necessary to limit detection as close as possible to light signals emanating from the analytes to be detected and to exclude interfering signals, such as ambient light, diffusively scattered or reflected excitation light from the signal acquisition. Therefore, its is advantageous, if a multi-facet prism as an optical component for beam deflection, as part of an analytical system according to the invention, comprises additional means for deflecting or masking reflections of the excitation light emanating from the sensor platform. It is also possible that one or more reflective facets of the multi-facet prism are partly or completely metallized.

The optical system according to the invention can comprise additional optical elements for the spectral selection of the excitation wavelength, such as interference filters or edge filters, and optionally additional optical elements for beam attenuation, such as optical neutral density or grey filters, optionally provided as a "continuously varying" filter with a continuous local gradient of the transmission, and/or further elements for beam guiding, such as glass fibers, optionally connected to micro lenses or diffractive optical elements, in the optical path of the excitation light between the at least one excitation light source and the optical component with several discrete facets for beam deflection.

Characteristic for a possible embodiment of the system is that two or more lasers with different emission wavelengths are used as excitation light sources.

Additional optical elements comprising, for example, diffractive optical elements and/or lenses for beam expansion and/or for generation of a parallel beam and/or diaphragms or masks for partial masking of the beam can be located in the optical path of the excitation light between the light sources and the sensor platform, in order to generate a desired beam profile on the sensor platform.

Characteristic for a preferred embodiment of the optical system according to the invention is, that the sensor platform comprises a multitude of discrete measurement areas, in which biological or biochemical or synthetic recognition elements for the determination of one or more analytes are immobilized. Thereby, up to 100,000 measurement areas can be provided in a two-dimensional arrangement on the sensor platform. A single measurement area can have an area of 0.001 mm$^2$-6 mm$^2$.

The simplest method of immobilization of the biological or biochemical or synthetic recognition elements consists in physical adsorption, for example due to hydrophobic interaction between the recognition elements and the base plate. However, the extent of these interactions can be affected strongly by the composition of the medium and its physical-chemical properties, such as polarity and ionic strength. Especially in case of sequential addition of different reagents in a multi-step assay, the adhesion of the recognition elements on the surface, after only adsorptive immobilization, is often insufficient. In a preferred embodiment of the optical system according to the invention, the adhesion is improved by deposition of an adhesion-promoting layer on the sensor platform for the immobilization of the biological or biochemical or synthetic recognition elements. Especially in case of biological or biochemical recognition elements to be immobilized, the adhesion-promoting layer can also contribute to improve the "biocompatibility", i.e. to preserve the binding capability of the recognition elements, in comparison with the binding capability of these recognition elements in their natural biological or biochemical environment, and to avoid a denaturation. It is preferred, that the adhesion-promoting layer has a thickness of less than 200 nm, preferably of less than 20 nm. For the generation of the adhesion-promoting layer, many materials can be used. Without any restriction, it is preferred, that the adhesion-promoting layer comprises one or more chemical compounds from the groups comprising silanes, epoxides, functionalized, charged or polar polymers, and "self-organized passive or functionalized mono- or double-layers".

A further important aspect of the optical system according to the invention is, that the biological or biochemical or synthetic recognition elements are immobilized in discrete (laterally separated) measurement areas. These discrete measurement areas can be formed by spatially selective deposition of the biological or biochemical or synthetic recognition elements on the sensor platform. Many methods can be used for the deposition. It is preferred without any restriction of generality, that the biological or biochemical or synthetic recognition elements are deposited on the sensor platform by one or more methods from the group of methods comprising "ink jet spotting, mechanical spotting by means of pin, pen or capillary, "micro contact printing", fluidically contacting the measurement areas with the biological or biochemical or synthetic recognition elements upon their supply in parallel or crossed micro channels, upon exposure to pressure differences or to electric or electromagnetic potentials, and photochemical or photolithographic immobilization methods.

As said biological or biochemical or synthetic recognition elements, components from the group comprising nucleic acids (e.g. DNA, RNA, oligonucleotides) and nucleic acid analogues (e.g. PNA), mono- or polyclonal antibodies, peptides, enzymes, aptamers, synthetic peptide structures, soluble membrane-bound proteins and proteins isolated from a membrane, such as receptors, their ligands, antigens for antibodies, "histidin-tag components" and their complex forming partners, cavities generated by chemical synthesis, for hosting molecular imprints. etc., are deposited. It is also intended that whole cells, cell components, cell membranes or their fragments are deposited as biological or biochemical or synthetic recognition elements.

In general, the immobilized recognition elements are selected in such a way, that they recognize and bind the analyte to be determined with a specificity as high as possible. Typically however, it must be expected that also a nonspecific adsorption of analyte molecules on the surface of the base plate does occur, especially if there are still empty sites between the recognition elements immobilized in the measurement areas. Therefore it is preferred, that regions between the laterally separated measurement areas are "passivated" for minimization of non-specific binding of analytes or their tracer compounds, i.e., that compounds, that are "chemically neutral" towards the analyte, are deposited between the laterally separated measurement areas (d), preferably for example out of the groups formed by albumins, especially bovine serum albumin or human serum albumin, casein, unspecific polyclonal or monoclonal, alien or empirically unspecific antibodies for the one or the multiple analytes to be determined (especially for immuno assays), detergents—such as Tween 20®—fragmented natural or synthetic DNA not hybridizing with polynucleotides to be analyzed, such as extract from herring or salmon sperm (especially for polynucleotide hybridization assays), or also uncharged but hydrophilic polymers, such as poly ethyleneglycols or dextranes.

The optical system according to the invention is typically characterized in that the luminescence light from the measurement areas on the sensor platform is directed onto at least one opto-electronic detector.

It is preferred that the luminescence light from the measurement areas is imaged onto a locally resolving detector, which is preferably selected from the group formed by CCD cameras, CCD chips, photodiode arrays, avalanche diode arrays, multi-channel plates and multi-channel photomultipliers.

There are various possibilities for the design of the detection beam path. As one possibility, the luminescence light from the measurement areas is imaged onto the at least one opto-electronic detector by means of a system comprising one or more lenses and/or mirrors. It is also possible that one or more optical elements for selection of the emission wavelength and discrimination of light of other wavelengths, such as diffractive elements, interference filters or edge filters, are provided in the emission beam path between the sensor platform and the at least one opto-electronic detector for recording the luminescence light emanating from the measurement areas.

It is preferred that the emission beam path has a divergence or convergence of less than 15° at the position of application of said optical element for the spectral selection. One possibility of the technical realization consists in that the optical elements for selection of the emission wavelength and for discrimination of light of other wavelengths, such as interference filters or edge filters, are located between the two halves of a tandem objective.

There are also various possibilities for the design of the sensor platform, as a part of the optical system according to the invention. The sensor platform can comprise an optically transparent support (supporting substrate), preferably of glass or a thermoplastic plastics, on which the biological or biochemical or synthetic recognition elements are immobilized in the measurement areas.

Under the nomenclature "optical transparency" it is thereby understood, that the material characterized by this property is essentially transparent and thus essentially free of absorption at least at one or more excitation wavelengths used for the excitation of one or more luminescences.

It is preferred that the sensor platform comprises a planar optical waveguide.

It is especially preferred that the sensor platform comprises an optical thin-film waveguide with a first optically transparent layer (a) on a second optically transparent layer (b), and wherein the optically transparent layer (b) has a lower refractive index than the optically transparent layer (a).

It is preferred that in-coupling of excitation light into the optically transparent layer (a) is performed using a diffractive grating (c) modulated in the layer (a). Preferably, the diffractive gratings modulated in layer (a) are relief gratings. A sensor platform as a part of the optical system according to the invention can comprise a single or also multiple discrete grating structures (c). Different grating structures (c) modulated in the optically transparent layer (a) of the sensor platform can have a common or also different grating periods.

Characteristic for a preferred embodiment of the sensor platform as part of the optical system according to the invention is, that grating structures (c) provided in the waveguiding layer (a) of the sensor platform are arranged in a one- or two-dimensional array, with even, non-modulated regions of the waveguiding layer (a) being adjacent to the grating structures in the direction of propagation of an excitation light to be in-coupled into the layer (a), and wherein arrays of two or more measurement areas are provided on these non-modulated regions, which can optionally additionally be fluidically sealed against each other in discrete sample compartments.

In order to allow for a controlled removal of the excitation light in-coupled into and guided in the layer (a) of the sensor platform and also to minimize a cross-talk of light signals between adjacent measurement areas or between adjacent arrays of measurement areas it is advantageous, if second grating structures (c') for the out-coupling of excitation light and, where appropriate, of luminescence light back-coupled into the waveguiding layer (a) are provided on the sensor platform, in addition to grating structures (c) for the in-coupling of excitation light, in order to out-couple again the light guided in the waveguiding layer (a), after its passing through the region the measurement areas (in direction of propagation of the guided excitation light following an in-coupling grating structure (c)). Thereby, grating structures (c) and (c') can have similar or also different grating periods.

Characteristic for one possible embodiment is, that grating structures (c) and optionally (c') are provided discretely for individual segments (arrangements in one- or two-dimensional arrays) of measurement areas.

It is preferred that grating structures (c) and optionally (c') are provided as continuous strips (columns) extending over the whole sensor platform perpendicular to the direction of propagation of the excitation light to be in-coupled.

Characteristic for a possible embodiment, especially for sequential measurements, is that grating structures (c') are also used as in-coupling gratings (c) upon sequential performance of measurements.

For certain applications, especially for achieving a very high density of measurement areas without an optical crosstalk of luminescences emanating from these measurement areas, it is preferred that grating structures (c) for the in-coupling and (c') for the out-coupling of light out of the waveguiding layer (a) of the sensor platform have the same period and are modulated continuously below all measurement areas of the sensor platform.

For a given thickness of the optically transparent layer (a) the sensitivity of the arrangement according to the invention is the better, the larger the difference between the refractive index of the layer (a) and the refractive indices of the surrounding media is, i.e., the larger the refractive index of the layer (a) in comparison to the adjacent layers is. It is preferred that the refractive index of the first optically transparent layer (a) is higher than 1.8.

A further important requirement on the properties of the layer (a) is, that the propagation losses of the light guided in said layer are as low as possible. It is preferred that the first optically transparent layer (a) comprises a material of the group of $TiO_2$, $ZnO$, $Nb_2O_5$, $Ta_2O_5$, $HfO_2$, or $ZrO_2$, especially preferred of $TiO_2$ or $Nb_2O_5$ or $Ta_2O_5$. Combinations of several such materials can also be used.

For a given material of the layer (a) and a given refractive index the sensitivity is the better, the smaller the layer thickness is, as long as the layer thickness is larger than a lower limiting value. The lower limiting value is determined by the cease of light-guiding upon decrease of the layer thickness below a value that is dependent on the wavelength of the light to be guided and by an increase of the propagation losses with decreasing layer thickness in case of very thin layers. It is of advantage, if the product of the thickness of layer (a) and its refractive index is one tenth up to a whole, preferably one third to two thirds of the excitation wavelength of an excitation light to be coupled into layer (a).

Characteristic for a special embodiment of the sensor platform, as a part of the optical system according to the invention, is that a thin metal layer, preferably of gold or silver, optionally on an additional dielectric layer with lower refractive index than layer (a), for example of silica or magnesium fluoride, is deposited between the optically transparent layer (a) and the immobilized biological or biochemical or synthetic recognition elements, wherein the thickness of the metal layer and of the optional additional intermediate layer is selected in such a way that surface plasmon can be excited at the excitation and/or the luminescence wavelength.

It is preferred that optically or mechanically recognizable marks for simplifying adjustments in an optical system and/or for the connection to sample compartments as part of an analytical system and/or as helps for a later image analysis are provided on the sensor platform, as a part of the optical system according to the invention.

For the routine-type handling of a multitude of sensor platforms, perhaps provided in different embodiments, as well as for the guarantee of a continuously high product quality, the retraceability of the history of manufacturing and use of a sensor platform is of high importance. Therefore it is preferred that the sensor platform, as a part of the optical system according to the invention, is provided with a mark, such as a barcode, which can be read by a barcode reader integrated into the optical system.

A variety of further embodiments of sensor platforms, which are suited as a part of an optical system according to the invention, are described in detail, for example in U.S. Pat. No. 5,822,472, No. 5,959,292, and No. 6,078,705, and in the patent applications WP 96/35940, WO 97/37211, WO 98/08077, WO 99/58963, PCT/EP 00/04869, and PCT/EP 00/07529. The embodiments of sensor platforms and of methods of determination of one or more analytes by luminescence detection are also part of the present invention upon use of an optical system according to the present invention.

In principle, an optical system according to the invention can be operated both with monochromatic and with polychromatic light sources. It is preferred, however, that the excitation light from the two or more light sources is always essentially monochromatic.

Characteristic for a special embodiment of the optical system according to the invention is, that the excitation light from different light sources is irradiated simultaneously from different directions towards the sensor platform in such a way, that the offset between the beam centers on the sensor platform is less than 0.2 mm.

The detection beam path of the optical system according to the invention can be designed in such a way, that optical components of the group comprising lenses or lens systems for the shaping of the transmitted light bundles, planar or curved mirrors for the deflection and optionally additional shaping of the light bundles, prisms for the deflection and optionally spectral separation of the light bundles, dichroic mirrors for the spectrally selective deflection of parts of the light bundles, neutral density filters for the regulation of the transmitted light intensity, optical filters or monochromators for the spectrally selective transmission of parts of the light bundles, or polarization selective elements for the selection of discrete polarization directions of the excitation or luminescence light are located between the sensor platform and the one or more detectors.

The light excitation can be performed continuously (cw). It is preferred, however, that the excitation light is launched in pulses with a duration of 1 fsec to 10 min.

Characteristic for an improvement of the optical system according to the invention is, that the emission light from the measurement areas is measured time-resolved.

It is preferred, that for referencing purposes light signals of the group comprising excitation light at the location of the light sources or after expansion of the excitation light or after its multiplexing into individual beams, scattered light at the excitation wavelength from the location of the one or more laterally separated measurement areas, and light of the excitation wavelength out-coupled by the grating structure (c) besides the measurement areas are measured. Thereby, the measurement areas for determination of the emission light and of the reference signal can overlap partly or completely, whereas preferably they are identical.

In general, the excitation beam path of the optical system according to the invention, concerning that part of the beam path until the launch of the excitation light onto said optical component with several discrete facets for beam deflection described above, is determined and fixed when the optical components are assembled and remains essentially unchanged thereafter, except for, e.g., thermally caused minor fluctuations. Therefore, it is also possible to measure once the distribution of the excitation light intensity in the beam path before said optical component for beam deflection and to store this distribution as a specific system function (instrument function) for purposes of referencing, which can be treated (taken into account) like a reference signal for a data correction. The measurement of this distribution of the excitation light can be repeated in adequate temporal intervals, if necessary, and be stored as a new instrument function.

When the emission beam profiles of the light sources and the optical properties of the optical components provided in the beam path are precisely known, it is even possible to calculate the distribution of the excitation light mathematically and store it as an instrument function, which can be treated (taken into account) like a reference signal for a data correction.

As described above, sensor platforms based on thin-film waveguides and on in-coupling of the excitation light by means of a diffractive grating modulated in the waveguiding layer are characterized by a resonance angle with an only very small half-width for the in-coupling. Especially for embodiments of the inventive optical systems with such type of sensor platforms it is advantageous, if the optimization of the adjustment for optimum in-coupling of excitation light by means of an in-coupling grating (c) towards measurement areas provided in direction of propagation of the in-coupled light is performed upon maximization of the excitation light out-coupled by an out-coupling grating (c') and measured by a detector, wherein this optimization is preferably performed under computer control.

Characteristic for a special embodiment of the optical system according to the invention is, that a rotation of the optical component with several discrete facets for beam deflection, around an axis located inside or outside of said optical component, is performed for the optimization of the adjustment of the coupling angle. Thereby it is preferred, that the optical component with several discrete facets for beam deflection is connected with a rotary element with axis of rotation inside or outside of said optical component in such a way, that the offset of the beam on the sensor platform is less than 0.3 mm upon a rotation of said optical component around said axis of rotation by less than 5°.

Characteristic for many possible embodiments of the optical system according to the invention is, that a translation of the sensor platform in parallel or perpendicular to the grating lines is performed for optimization of the coupling position.

It is preferred, that the optimization of the adjustment is performed upon maximization of one or more reference signals from one or more measurement areas on the sensor platform, wherein this optimization is preferably performed under computer control.

Thereby, it is characteristic for one possible embodiment, that said reference signal is scattered light of the excitation wavelength. However, it is also possible that said reference signal is luminescence light from measurement areas dedicated for purposes of referencing and/or of adjustment.

In one embodiment of the optical system according to the invention, light irradiation and acquisition of the emission light from a plurality of measurement areas or from on or from multiple arrays of measurement areas or even from all measurement areas are performed simultaneously. Characteristic for another embodiment is, that the irradiation of the excitation light to and detection of emission light from one or more measurement areas is performed sequentially for one or more measurement areas. It is also possible, sequential irradiation of the excitation light and detection of the emission light from one or more measurement areas is performed multiple times (for these measurement areas).

In case of sequential detection of luminescence from different measurement areas a locally resolving detector is not mandatory, but in this case a simple detector, such as a conventional photomultiplier or a photodiode or an avalanche photodiode can be used.

Characteristic for another embodiment of an optical system according to the invention is, that such inventive arrangement is moved between steps of sequential excitation and detection.

A further subject of the invention is an analytical system, for the determination of one or more analytes in at least one sample on one or more measurement areas on a sensor platform by luminescence detection, comprising an optical system according to the invention and according to any the embodiments disclosed above and supply means for bringing the one or more samples into contact with the measurement areas on the sensor platform.

Thereby it is preferred that the analytical system according to the invention additionally comprises one or more sample compartments, which are at least in the area of the one or more measurement areas or of the measurement areas combined to segments open towards the sensor platform. Thereby the sample compartments can have a volume of 0.1 nl-100 µl each.

Characteristic for a preferred embodiment of the analytical system according to the invention is, that the sample compartments are closed, except for inlet and/or outlet openings for the supply or outlet of samples, at their side opposite to the optically transparent layer (a), and wherein the supply or the outlet of the samples and optionally of additional reagents is performed in a closed flow-through system, wherein, in case of liquid supply to several measurement areas or segments with common inlet and outlet openings, these openings are preferably addressed row by row or column by column.

Another possible embodiment consists in that the supply of the samples and optionally of additional reagents is performed in parallel or crossed micro-channels, upon exposure to pressure differences or to electric or electromagnetic potentials.

Characteristic for another preferred embodiment of the analytical system according to the invention is, that the sample compartments are provided with openings at the side facing away from the optically transparent layer (a), for locally addressed supply or removal of the samples or of other reagents.

It is preferred, that the sample compartments are arranged in an array, comprising the sensor platform as the base plate and a body combined therewith in such a way, that an array of cavities is generated between the base plate and said body, for generation of an array of flow cells fluidically sealed against each other, and that at least one outlet of each flow cell leads to a reservoir fluidically connected with said flow cell and capable to receive liquid exiting from said flow cell. Thereby it is advantageous, if the reservoir for receiving liquid exiting from the flow cell is provided as a recess in the exterior wall of the body combined with the base plate.

The analytical system according to the invention can principally comprise almost any number of sample compartments, typically 2-2000, preferably 2-400, most preferably 2-100 sample compartments.

It is preferred, that the pitch (geometrical arrangement in rows and/or columns) of the inlets of the sample compartments does correspond to the pitch (geometrical arrangement) of the wells of a standard microtiter plate.

It is also preferred, that the arrangement of sample compartments with the sensor platform as the base plate and the body combined therewith does correspond to the footprint of a standard microtiter plate.

Characteristic for another embodiment of the analytical system according to the invention with, for example, 2 to 8 sample compartments in a column or, for example, 2 to 12 sample compartments in a row, is that said sample compartments in a column or row themselves are combined with a carrier ("meta-carrier") with the dimensions of standard microtiter plates in such a way, that the pitch (geometrical arrangement in rows and/or columns) of the inlets of the flow cells does correspond to the pitch (geometrical arrangement) of the wells of a standard microtiter plate.

Characteristic for a further variant of the analytical system according to the invention is, that a removable bottom protection is provided below the sensor platform as the base plate of an arrangement of sample compartments, and wherein optionally the upper side of the arrangement of sample compartments is closed with an additional covering top, for example a film, a membrane or a cover plate. Thereby it is preferred, that the bottom protection is removed automatically or semi-automatically before a measurement is started.

A preferred embodiment of an analytical system according to the invention, comprising an optical system according to any of the disclosed embodiments, is characterized in that at least one grating structure (c) modulated in the waveguiding layer (a) of a sensor platform as the base plate, for the in-coupling of excitation light towards the measurement areas, is provided within each sample compartment.

Characteristic for one possible embodiment is, that grating structures (c) are provided within the range of the sample compartments and additional grating structures (c') for light out-coupling are always arranged outside of those sample compartments where the in-coupling is performed.

Characteristic for another possible embodiment of the analytical system according to the invention is, that grating structures (c) and optional additional grating structures (c') extend over the range of several or of all sample compartments.

It is preferred, that 5-5000, preferably 10-400 measurement areas are provided in one sample compartment.

Characteristic for an improvement of the analytical system according to the invention is, that additionally mechanical means and a transport mechanism are provided, operable for an automated transport of an arrangement of sample compartments, comprising a sensor platform as a base plate and a body combined therewith, from a location of the insertion of that arrangement to the location of luminescence excitation and detection and optionally from there back to the original position.

Another improvement consists in that said analytical system additionally comprises a receiving device ("stacker") for receiving a plurality of arrangements of sample compartments.

Thereby it is preferred that the loading of the "stacker" from the position of the insertion of the arrangement of sample compartments and the transport of said arrangement of sample compartments from there to the location of luminescence excitation and detection and then back to the original location is performed automatically.

Characteristic for another embodiment of the analytical system according to the invention is, that said analytical system comprises one or more temperature-controllable zones. Thereby it is preferred, that the arrangement of sample compartments and/or the excitation light sources and/or the one or more opto-electronic detectors and/or the "stacker" can be temperature-controlled separately. This allows, for example, to cool biological samples until the moment and thus to prevent or reduce a possible degradation of contained components. The signal stability of opto-electronic devices is also generally effected in a positive way by temperature control.

Characteristic for another variant of the analytical system according to the invention is, that the arrangement of sample compartments and/or the excitation light sources and/or the one or more opto-electronic detectors and/or the "stacker" are operated under a higher air pressure than ambient pressure. Thus can, for example, the penetration of dust into the system be prevented.

For the various embodiment of the analytical system according to the invention it is preferred, that said analytical system additionally comprises one or more electronic control components for control of the status of one or more optical or electrical or mechanical components, which control components can generate an optical or acoustic or electronic alarm signal if necessary.

It is also advantageous, if the analytical system according to the invention comprises means for preventing the insertion of not adequate sensor platforms, for example with wrong mechanical dimensions.

For the conduction of a large number of studies and measurements and for improvement of their reproducibility, a high degree of automation is generally desirable. Therefore it is preferred, that the analytical system according to the invention additionally comprises one or more electronic processors, connected to storage media and electronic connecting media, a keyboard for data or command input, a screen and a program code for automated operation.

Especially for routine-type working processes it is also preferred, that the operation of said analytical system and/or the measurement are performed automatically using pre-defined files for initialization. It is advantageous, if the analytical system according to the invention is reset automatically to a pre-defined initial status and possibly generated measurement data are secured in a file, when an indicated error function has occurred.

Characteristic for an improvement of the analytical system according to the invention is, that a file is generated automatically for each measurement, in which file are stored the code of the used sensor platform, the essential measurement parameters and the measurement data.

Characteristic for another advantageous improvement is, that local variations of the excitation light intensity on the sensor platform and/or of the detection sensitivity of the optical system for light signals from different positions on the sensor platform are corrected using means which comprise, for example, the recording of images for correction taken at the excitation wavelength and/or at one or more luminescence wavelengths, the calculation of theoretical distributions of the available excitation light intensity, theoretical calculations of the locally resolved efficiency of the optical imaging and detection system, etc.

A further subject of the invention is a method for the determination of one or more analytes by luminescence detection, upon using an analytical system according to the invention which comprises an optical system according to the invention, wherein one or more liquid samples to be analyzed for the one or more analytes are brought into contact with one or more measurement areas on the sensor platform, excitation light is directed towards the measurement areas, thus exciting compounds capable of luminescence in the sample or on the measurement areas to luminescence and the emitted luminescence is measured.

The method according to the invention includes, that, for generation of luminescence, at least one luminescent dye or luminescent nanoparticle is used as a luminescence label, which can be excited and emits at a wavelength between 300 nm and 1100 nm.

Characteristic for an advantageous embodiment of the method is, that it comprises means to extend the dynamic range for signal recording by at least a factor of 3.

Said means for extending the dynamic range can comprise, for example, the application of differently long exposure times, i.e., the duration of the irradiation of the excitation light and the integration time of the detector, which exposure times can be varied by at least a factor of 3.

As another possibility, the means for extending the dynamic range can comprise a variation of the excitation light available on the sensor platform by at least a factor of 3, for example upon using discrete neutral density filters in the excitation beam path, optionally provided as a "continuously varying" filter with a continuous local gradient of the transmission, or upon variation of the intensity of the light sources or upon changing the adjustment of the sensor platform with respect to the excitation beam path.

In general, it is characteristic for the method according to the invention, that the at least one luminescence label is bound to the analyte or, in a competitive assay, to an analyte analogue or, in a multi-step assay, to one of the binding partners of the immobilized biological or biochemical or synthetic recognition elements or to the biological or biochemical or synthetic recognition elements.

Characteristic for an improvement of the method is, that a second or more luminescence labels of similar or different excitation wavelength as the first luminescence label and similar or different emission wavelength are used.

Characteristic for another possible embodiment of the method according to the invention is, that charge or optical energy transfer from a first luminescent dye acting as a donor to a second luminescent dye acting as an acceptor is used for the detection of the analyte.

Characteristic for another advantageous embodiment of the method is, that the one or more luminescences and/or determinations of light signals at the excitation wavelengths are performed polarization-selective. Thereby it is preferred, that the one or more luminescences are measured at a polarization that is different from the one of the excitation light.

The method according to the invention is suited for the simultaneous or sequential, quantitative or qualitative determination of one or more analytes of the group comprising antibodies or antigens, receptors or ligands, chelators or "histidin-tag components", oligonucleotides, DNA or RNA strands, DNA or RNA analogues, enzymes, enzyme cofactors or inhibitors, lectins and carbohydrates.

It is also characteristic for possible embodiments of the method, that the samples to be examined are naturally occurring body fluids, such as blood, serum, plasma, lymph or urine, or egg yolk or optically turbid liquids or tissue fluids or surface water or soil or plant extracts or bio- or process broths, or are taken from biological tissue fractions or from cell cultures or cell extracts.

A further subject of the invention is the use of an optical system according to the invention and/or of an analytical system according to the invention and/or of a method according to the invention for the quantitative or qualitative analyses for the determination of chemical, biochemical or biological analytes in screening methods in pharmaceutical research, combinatorial chemistry, clinical and pre-clinical development, for real-time binding studies and for the determination of kinetic parameters in affinity screening and in research, for qualitative and quantitative analyte determinations, especially for DNA- and RNA analytics, for generation of toxicity studies and for the determination of gene and protein expression profiles, and for the determination of antibodies, antigens, pathogens or bacteria in pharmaceutical product development and research, human and veterinary diagnostics, agrochemical product development and research, for symptomatic and pre-symptomatic plant diagnostics, for patient stratification in pharmaceutical product development and for the therapeutic drug selection, for the determination of pathogens, nocuous agents and germs, especially of salmonella, prions and bacteria, in food and environmental analytics.

The invention is further explained by the following examples.

EXAMPLE 1

1A: Sensor Platform

A sensor platform with the exterior dimensions of 75 mm width×113.5 mm length×0.7 mm thickness is used, on the surface of which 96 micro flow cells, with inside dimensions of 8 mm width×8 mm length×0.15 mm height, in the pitch (arrangement in rows and columns) of a classical microtiter plate (Pitch: 9 mm) can be arranged, by combination of said sensor platform with a polycarbonate plate having open recesses facing the sensor platform. The polycarbonate plate can be glued to the sensor platform in such a way, that the recesses are then tightly sealed against each other.

The substrate material (optically transparent layer (b)) consists of AF 45 glass (refractive index n=1.52 at 633 nm). A periodic sequence (screen) of pairs of in- and out-coupling gratings, with grating lines (318 nm period) in parallel to the width of the sensor platform, with a grating depth of 12+/−3 nm, is generated in the substrate, wherein the grating lines extend over the whole width of the sensor platform. The distance between subsequent grating pairs is 9 mm; the length of the individual grating structures (in parallel to the length of the sensor platform) is 0.5 mm. The distance between the in- and the out-coupling grating of a grating pair is 5.5 mm, allowing for in- and out-coupling of the excitation light always within the (inside) region of the sample compartments, after combination of the sensor platform with the polycarbonate plate described above. The waveguiding, optically transparent layer (a) of $Ta_2O_5$ on the optically transparent layer (b) has a refractive index of 2.15 at 633 nm (layer thickness 150 nm).

The sample compartments formed by the combination of the sensor platform with the polycarbonate plate are provided with conically bored openings at the demarcation surface opposite to the sensor platform, thus allowing for a filling or clearing of the sample compartments by inserting standard-type, commercially available pipette tips of polypropylene.

As a preparation for the immobilization of the biochemical or biological or synthetic recognition elements, the senor platforms are cleaned with chloroform in an ultrasonic apparatus, chemically activated by a silanization reaction with glycidyloxypropyltrimethoxy silane, and thus prepared for the immobilization of the probe cDNAs as biological recognition elements. The individual cDNAs, at a concentration of 50 ng/µl, are deposited as spots of 10 drops (0.1 nl) each, using a commercial, piezo-controlled micropipette (GeSIM, Großerkmannsdorf, DE), resulting in spots as discrete measurement areas of about 150 µm.

In a 10×10 spot arrangement (array of 100 features), always 4 measurement areas with the same cDNA are provided in a way that, at the end of the immobilization step, an array always comprises measurement areas with 25 different recognition elements with four replicates for each recognition element. The spots are provided at a distance (center-to-center) of 400 µm. Thus, an individual array covers an area of about 4×4 $mm^2$, wherein the area is arranged at short distance (about 2 mm) to a grating structure (c), which is used in the later analytical detection method as the in-coupling grating for the excitation light. For the later analysis of a plurality of samples on identical arrays, a multitude of identical arrays is generated on the sensor platform at a pitch of 9 mm in a way as described above.

The described polycarbonate plate is combined with the prepared sensor platform in such a way, that the individual sample compartments are fluidically tightly sealed against each other and that the arrays with the corresponding in-coupling gratings (c) are always located within the sample compartments.

1B: Optical Beam Path

Figure 1:
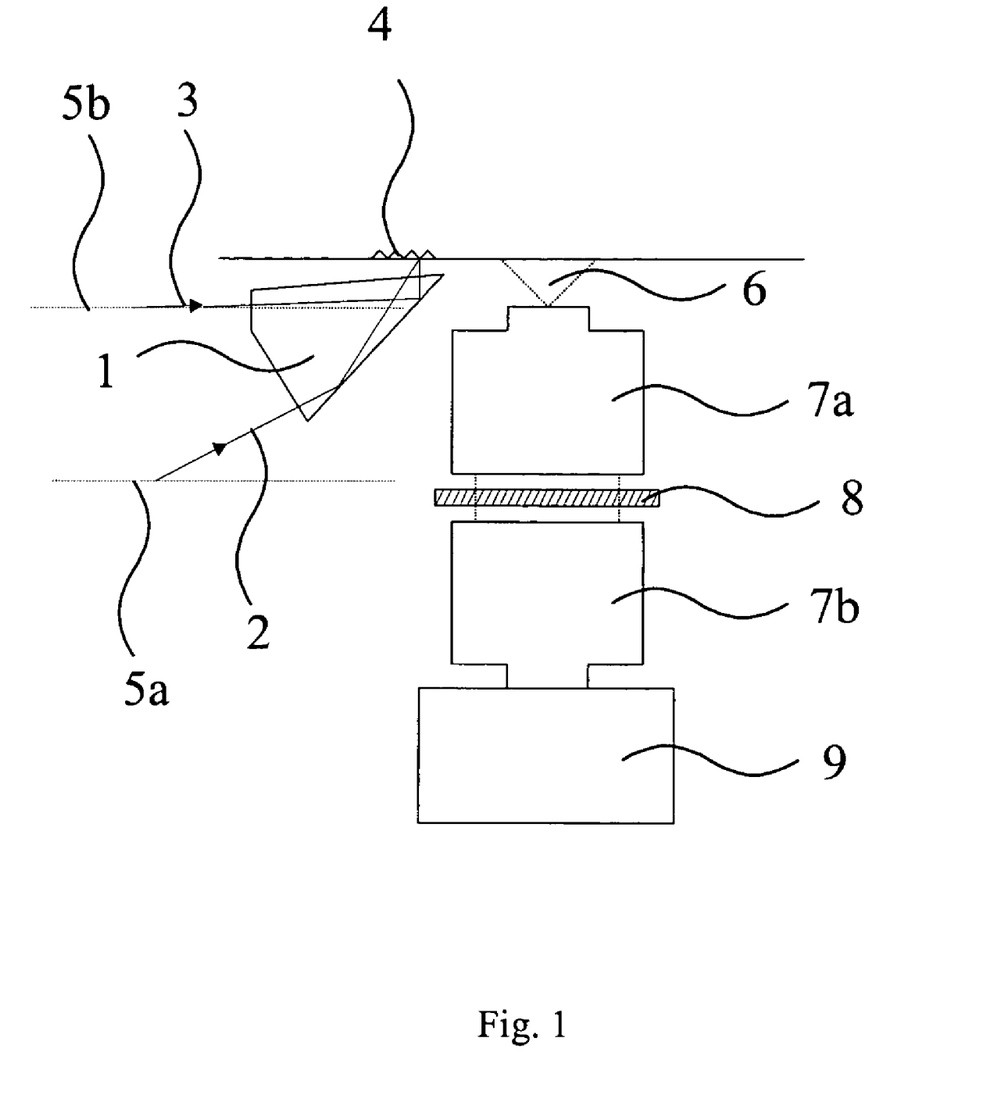
FIG. 1 is an illustration of the sensor platform.

The beam path for excitation light of different wavelength, passing through an optical component for beam deflection and propagating towards the in-coupling grating of a sensor platform, is shown schematically, i.e. not according to scale and not isogonal, in FIG. 1.

A multi-facet prism, as an example of an optical component with several discrete facets for beam deflection, is denoted with (1). (2) indicates the beam path of shorter-wavelength, e.g. blue excitation light through the lower facet towards the in-coupling grating (4) (corresponding to a grating structure (c) according to the above disclosure of the invention) of the sensor platform, (3) denotes the beam path of a longer-wavelength, e.g. red excitation light.

With the layer and grating parameters of the sensor platform described in Example 1A, the in-coupling angle for excitation light of 492 nm is about +18.2° and for excitation light of 670 nm about −17.4° (with air as the medium above the coupling grating). Consequently, the divergence angle between light beams of these excitation wavelengths is 35.6°, when the corresponding in-coupling conditions are satisfied. The multi-facet prism, as a part of the optical system according to the invention, is designed in such a way that, before entrance of the light into the prism, the angle between the irradiated short-wavelength excitation light and the plane (5a) parallel to the plane of the sensor platform surface is 27.3°, whereas, before entrance of the light into the prism, the angle between the irradiated long-wavelength excitation light and the plane (5b) parallel to the sensor platform surface is 1.9°. Consequently, the original angular divergence, before entrance of the light beams into the prism, is only 25.9°. Thus, the divergence angle is increased, in this example, by a factor of 1.37, by using the multi-facet prism as part of the optical system according to the invention. Additionally, the excitation light beams of both wavelengths hit the in-coupling grating (4) on the sensor platform at the same location. Thus, an in-coupling without a change of the position of the sensor platform is enabled.

The multi-facet prism is mounted on a goniometer (not shown in FIG. 1) in such a way, that a rotation by less than 5° leads to an offset of the beam centers on the sensor platform below 0.3 mm.

Additionally, the angle of beam spread (6), under which maximum angle luminescence light emanating from the sensor platform can be imaged onto the detector (9) by means of a tandem objective with an entrance objective (7a) and an exit objective (7b), is schematically indicated in FIG. 1. One or more interference filters (8) for spectral selection of the detection wavelength are located between the two halves of the tandem objective, in that part of the emission beam path with is parallel in the ideal case. By means of this arrangement a part of the isotropically emitted light emanating from the sensor platform is collected and directed onto the detector (9).

1C: Analytical System

Figure 2:
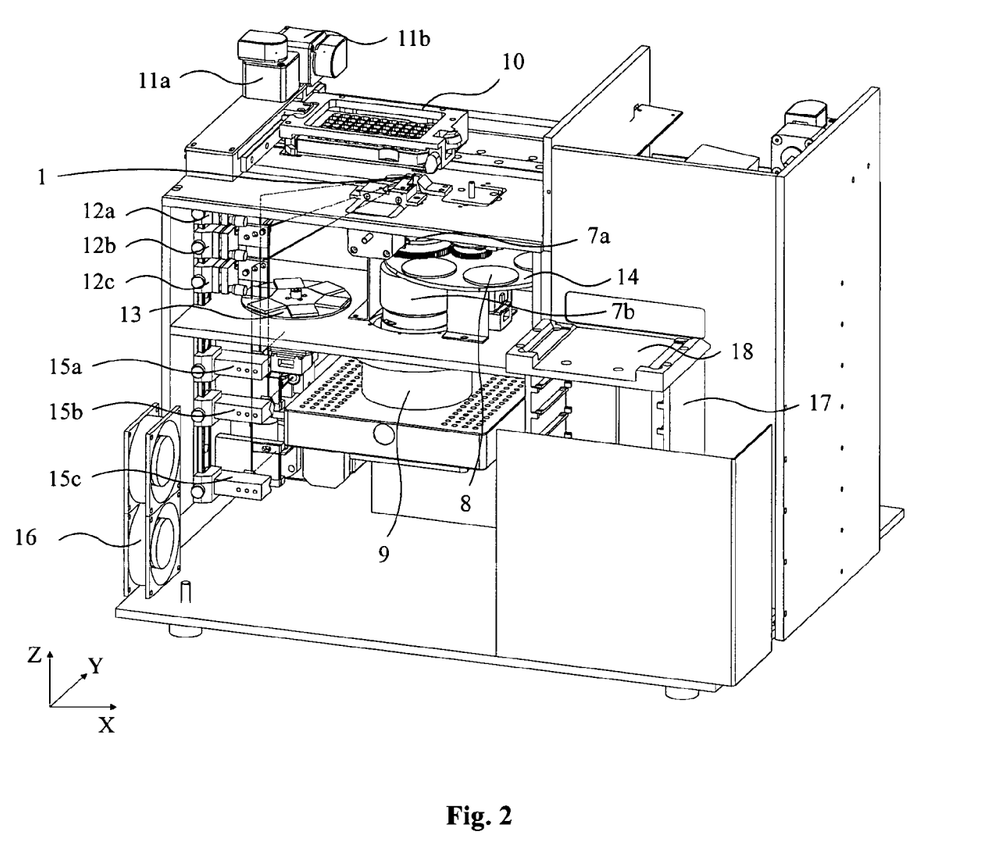
FIG. 2 is an illustration of the optical system comprising the sensor platform.

Parts of an exemplary embodiment of an analytical system according to the invention, including essential components of an optical system according to the invention, are shown in FIG. 2. The spatial directions x/y/z are indicated in the figure.

With (10) is shown in the most upper part of FIG. 2 an inventive device comprising a sensor platform and sample compartments provided in the embodiment with the external dimensions of a microtiter plate, which device can be moved in x-direction and y-direction, with respect to the direction of propagation of the excitation light, by means of stepping motors (11a, 11b). Separated from ambience by a sheet-metal hood, this part of the analytical system can be temperature-controlled separately.

Adjacent below is located a further section, comprising a row of mirrors with the corresponding mounts and adjustment means, 12a, 12b, 12c, for the deflection of the excitation light, preferably from laser light sources, towards one of the entrance facets of a multi-facet prism 1. During assembly of the system, the mirrors 12a-c are adjusted to the required direction of light irradiation onto the dedicated entrance facet of the multi-facet prism in a way that, after passing of the beam through the multi-facet prism, the resonance condition for the corresponding excitation wavelength, for in-coupling of said excitation light into the waveguiding layer of a sensor platform by means of a grating structure (4) can be satisfied. In case of necessary service, these mirrors can be adjusted in x- and y-direction. In each of the beam paths between mirrors 12a-c and the multi-facet prism are provided diaphragms (not shown in FIG. 2), which can be used to limit the excitation light bundle to the desired geometrical dimensions. Additionally, a filter wheel (13), for regulating the excitation light intensity by means of discrete neutral density filters of different transmissions, is provided in this section. In case of (spectrally) broad-band excitation light sources or upon use of lasers with multiple emission lines, one or more positions in the filter wheel 13 can also be used for interference filters or for edge filters of adequate transmission wavelength.

At the right part of this section is located a further filter wheel (14) for the selection of those wavelengths, at which the signal acquisition of the light emanating from the sensor platform shall be performed, using interference filters (8). Signal acquisition can be performed both at the emission wavelengths of the excited one or more luminescences and at emission wavelengths of the excitation light sources, optionally combined with the use of neutral density filters for attenuation of the light intensity. In an exemplary embodiment of the system the measurement of the light at the excitation wavelengths emanating from the sensor platform is performed using preferably narrow-band filters (i.e. <10 nm width of transmission) with the following central transmission wavelengths:

A) 635 nm (laser emission wavelength: 635 nm)
B) 532 nm (laser emission wavelength: 532 nm)
C) 492 nm (laser emission wavelength: 492 nm).

In case of weak luminescences, the intensity of which is negligible in comparison to the excited luminescence, the use of spectrally selective filters for light at the excitation wavelength is dispensable. It is also possible to avoid the risk of a saturation of the detector (9) by recording signals at the excitation wavelength using shorter exposure times and/or a reduced excitation light intensity by means of an adequate neutral density filter in the filter wheel 13. Then the use of filters in the filter wheel 14, for detection at the excitation wavelength, can also be dispensable.

For detection of the luminescence light excited at the wavelengths denoted under A) to C) the corresponding filters D)-F) are used:
D) filter for signal acquisition from luminescence in the range from 650-700 nm, excited at 635 nm
E) filter for signal acquisition from luminescence in the range from 540-590 nm, excited at 532 nm
F) filter for signal acquisition from luminescence in the range from 500-550 nm, excited at 492 nm Above the filter wheel (14) is located the entrance objective (7a) of a tandem objective, below the filter wheel the exit objective (7b) of a tandem objective.

In the section below are located mirrors 15a, 15b, and 15c, for the deflection of the excitation light which is preferably irradiated directly onto these mirrors. These mirrors 15a-c are preferably mounted with an offset with respect to each other and adjusted in such a way, that the excitation light with the adequate spatial direction is directed onto the corresponding mirrors 12a-c in a way to allow to satisfaction of the resonance condition for the corresponding excitation wavelength, for in-coupling of said excitation light into the waveguiding layer of a sensor platform by means of a grating structure (4). The exemplary arrangement of the mirrors 12a-c and 15a-c allows, in especial, also the simultaneous irradiation of excitation of different wavelengths, if the beam offset between these excitation lights on the sensor platform is sufficiently small. (Thereby an expansion of the arrangement to a larger number of light sources and to additional optical components for beam deflection is part of the present invention). In case of necessary service the mirrors 15a-c can be adjusted in z-direction.

Of course all mirrors mentioned above can be substituted, with respect to their function, by other beam-deflecting optical components, such as prisms.

The whole part of this section shown on the right, which is preferably temperature-controlled separately, is occupied in this exemplary embodiment by the detector (9), which is preferably a locally resolving detector, whereby a CCD camera is specially preferred.

The excitation light sources (not shown in the figure), from where, at a part of this section masked in this embodiment, the excitation light is emitted, are adjusted in such a way that the light beams arrive at the mirrors 15a-c at the adequate spatial orientation, that, after beam path through the other optical elements in the excitation light path described above, the resonance condition for the corresponding excitation wavelength, for in-coupling of said excitation light into the waveguiding layer of a sensor platform by means of a grating structure (4) can be satisfied.

In an exemplary embodiment of the system lasers or laserdiodes with main emission wavelengths at 635, 532, and 492 nm are used.

With (16) is denoted in the left lower part of the bottom section an arrangement of ventilators, which are used for air supply to the system or for removal of air from the system, especially to enable or facilitate the temperature control of the different segments of the system.

On the right side of FIG. 2 is shown a stacker (17), which can accommodate a plurality of inventive sensor platforms respectively of assemblies of sensor platforms and corresponding sample compartments, especially to enable the sequential conduction of a multitude of measurements. Preferably, this stacker is designed for accommodating such components with external dimensions of standard microtiter plates. The insertion of the components is performed at the insertion region (18), which additionally comprises a cover and a device for removing an optional bottom protection of the inventive sensor platform (not shown in this figure). By means of a photo sensor (also not shown) located in the insertion region it is controlled, if there is a sensor platform provided, if said sensor platform meets the external dimensions acceptable for the system, and if the sensor platform has been inserted at the correct orientation into the insertion region.

The section of the stacker can also be temperature-controlled separately, if necessary. The insertion of the sensor platforms into the insertion region (18) can be performed manually or also under computer control using an adequate robotic arm.

The invention claimed is:

1. An optical system for luminescence determination, comprising at least two excitation light sources, a sensor platform which comprises a multitude of discrete measurement areas, and an optical component with several discrete facets for deflecting a light beam arranged such that the angle of divergence between excitation light falling onto different facets of said optical component is increased or reduced by at least a factor of 1.2 in the optical path departing from said optical component, in comparison to the original divergence angle between said light rays irradiated onto said different facets, whereby said sensor platform is a planar optical waveguide and said planar optical waveguide comprises a first optically transparent layer on a second optically transparent layer and wherein the second optically transparent layer has a lower refractive index than the first optically transparent layer which comprises at least one first diffractive grating structure modulated therein for in-coupling of excitation light and the sensor platform is characterized by a coupling angle wherein resonance condition for in-coupling into the first optically transparent layer is met.

2. The optical system according to claim 1, wherein the angle of divergence between excitation light falling onto different facets of said optical component is increased by at least a factor of 1.2 in the optical path departing from said optical component, in comparison to the original divergence angle between said light rays irradiated onto said different facets.

3. The optical system according to claim 1, wherein said optical component with several discrete facets for beam deflection is a multi-facet mirror with planar or curved facets, preferably with planar facets.

4. The optical system according to claim 1, wherein said optical component with several discrete facets for beam deflection is a multi-facet prism with planar or curved facets.

5. The optical system according to claim 1, wherein the light from two or more excitation light sources of similar or different wavelength falls onto the same facet of said optical component for beam deflection.

6. The optical system according to claim 1, wherein a dedicated facet of said optical component is provided for each different excitation wavelength, the excitation light of said excitation wavelength to be directed onto the corresponding dedicated facet for beam deflection.

7. The optical system according to claim 1, wherein the beam deflection of excitation light of different wavelength into different predefined directions occurs with an offset of less than 0.2 mm between the centers of the deflected beams on the sensor platform.

8. The optical system according to claim 4, wherein the multi-facet prism comprises additional means for deflecting or masking reflections of the excitation light emanating from the sensor platform.

9. The optical system according to claim 4, wherein one or more reflective facets of the multi-facet prism are partly or completely metallized.

10. The optical system according to claim 1, wherein additional optical elements for the spectral selection of the excitation wavelength are located in the optical path of the excitation light between the at least one excitation light source and the optical component with several discrete facets for beam deflection.

11. The optical system according to claim 1, wherein two or more lasers with different emission wavelengths are used as excitation light sources.

12. The optical system according to claim 1, wherein additional optical elements comprising diffractive optical elements and/or lenses for beam expansion and/or for generation of a parallel beam and/or diaphragms or masks for partial masking of the beam are located in the optical path of the excitation light between the light sources and the sensor platform, in order to generate a desired beam profile on the sensor platform.

13. The optical system according to claim 1, wherein in the multitude of discrete measurement areas biological or biochemical or synthetic recognition elements for the determination of one or more analytes are immobilized.

14. The optical system according to claim 1, wherein up to 100,000 measurement areas are provided in a two-dimensional arrangement on the sensor platform.

15. The optical system according to claim 1, wherein a single measurement area has an area of 0.001 $mm^2$-6 $mm^2$.

16. The optical system according to claim 13, wherein an adhesion-promoting layer is deposited between the biological or biochemical or synthetic recognition elements and the sensor platform.

17. The optical system according to claim 16, wherein the adhesion-promoting layer has a thickness of less than 200 nm, and wherein the adhesion-promoting layer comprises a chemical compound of the groups comprising silanes, epoxides, functionalized, charged or polar polymers, and "self-organized passive or functionalized mono- or double-layers".

18. The optical system according to claim 13, wherein the multitude of discrete measurement areas are laterally separated and are generated on the sensor platform by laterally selective deposition of the biological or biochemical or synthetic recognition elements on said sensor platform.

19. The optical system according to claim 13, wherein, as said biological or biochemical or synthetic recognition elements, components of the group formed by nucleic acids and nucleic acid analogues, mono- or polyclonal antibodies, peptides, enzymes, aptamers, synthetic peptide structures, soluble membrane-bound proteins and proteins isolated from a membrane, receptors, their ligands, antigens for antibodies, "histidin-tag components" and their complex forming partners, cavities generated by chemical synthesis, for hosting molecular imprints.

20. The optical system according to claim 13, wherein whole cells, cell components, cell membranes or their fragments are deposited as biological or biochemical or synthetic recognition elements.

21. The optical system according to claim 18, wherein regions between the laterally separated measurement areas are "passivated" for minimization of non-specific binding of analytes or their tracer compounds.

22. The optical system according to claim 1, wherein the luminescence light from the measurement areas on the sensor platform is directed onto at least one opto-electronic detector.

23. The optical system according to claim 1, wherein the luminescence light from the measurement areas is imaged onto a locally resolving detector.

24. The optical system according to claim 1, wherein the luminescence light from the measurement areas is imaged onto the at least one opto-electronic detector by means of a system comprising one or more lenses and/or mirrors.

25. The optical system according to claim 1, wherein one or more optical elements for selection of the emission wavelength and discrimination of light of other wavelengths are provided in the emission beam path between the sensor platform and the at least one opto-electronic detector for recording the luminescence light emanating from the measurement areas.

26. The optical system according to claim 25, wherein the emission beam path has a divergence or convergence of less than 15° at the position of application of said optical element for the spectral selection.

27. The optical system according to claim 25, wherein the optical elements for selection of the emission wavelength and for discrimination of light of other wavelengths are located between the two halves of a tandem objective.

28. The optical system according to claim 1, wherein the sensor platform comprises an optically transparent support on which the biological or biochemical or synthetic recognition elements are immobilized in the measurement areas.

29. The optical system according to claim 1, wherein the first diffractive grating structures are modulated in the first optically transparent layer of the sensor platform being arranged in a one- or two-dimensional array, with even, non-modulated regions of the first optically transparent layer being adjacent to the first diffractive grating structures modulated therein in the direction of propagation of an excitation light to be in-coupled into the first optically transparent layer, and wherein arrays of two or more measurement areas are provided on these non-modulated regions.

30. The optical system according to claim 1, wherein second diffractive grating structures for the out-coupling of excitation light are provided on the sensor platform, in addition to first diffractive grating structures for the in-coupling of excitation light, in order to out-couple again the light guided in the first optically transparent layer, after its passing through the region of the measurement areas in direction of propagation of the guided excitation light following an in-coupling first diffractive grating structure.

31. The optical system according to claim 1, wherein the first diffractive grating structures and optionally second diffractive grating structures are provided discretely for individual segments by arrangement in one- or two-dimensional arrays of measurement areas.

32. The optical system according to claim 1, wherein the first diffractive grating structures are provided as continuous strips (columns) extending over the whole sensor platform perpendicular to the direction of propagation of the excitation light to be in-coupled.

33. The optical system according to claim 30, wherein the second diffractive grating structures are also used as in-coupling first diffractive gratings upon sequential performance of measurements.

34. The optical system according to claim 30, wherein the first diffractive grating structures for the in-coupling and second diffractive grating structures for the out-coupling of light out of the first optically transparent layer of the sensor platform have the same period and are modulated continuously below all measurement areas of the sensor platform.

35. The optical system according to claim 1, wherein the product of thickness of the first optically transparent layer times its refractive index is one tenth up to a whole of the wavelength of any excitation light to be coupled into the first optically transparent layer.

36. The optical system according to claim 13, wherein a thin metal layer is deposited between the first optically transparent layer and the immobilized biological or biochemical or synthetic recognition elements, wherein the thickness of the metal layer is selected in such a way that surface plasmon can be excited at the excitation and/or the luminescence wavelength.

37. The optical system according to claim 1, wherein optically or mechanically recognizable marks for simplifying adjustments in an optical system and/or for the connection to sample compartments as part of an analytical system and/or as helps for a later image analysis are provided on the sensor platform.

38. The optical system according to claim 1, wherein the excitation light from the two or more light sources is essentially monochromatic.

39. The optical system according to claim 1, wherein the excitation light from different light sources is irradiated simultaneously from different directions towards the sensor platform in such a way, that the offset between the beam centers on the sensor platform is less than 0.2 mm.

40. The optical system according to claim 1, wherein optical components of the group comprising lenses or lens systems for the shaping of the transmitted light bundles, planar or curved mirrors for the deflection, prisms for the deflection, dichroic mirrors for the spectrally selective deflection of parts of the light bundles, neutral density filters for the regulation of the transmitted light intensity, optical filters or monochromators for the spectrally selective transmission of parts of the light bundles, or polarization selective elements for the selection of discrete polarization directions of the excitation or luminescence light are located between the sensor platform and the one or more detectors.

41. The optical system according to claim 1, wherein the excitation light is launched in pulses with a duration of 1 fsec to 10 min.

42. The optical system according to claim 1, wherein the emission light from the measurement areas is measured time-resolved.

43. The optical system according to claim 1, wherein for referencing purposes light signals of the group comprising excitation light at the location of the light sources or after expansion of the excitation light or after its multiplexing into individual beams, scattered light at the excitation wavelength from the location of the one or more discrete measurement areas, and light of the excitation wavelength out-coupled by the at least one first diffractive grating structure besides the measurement areas are measured.

44. The optical system according to claim 43, wherein the measurement areas for determination of the emission light and of the reference signal do partly or completely overlap.

45. The optical system according to claim 30, wherein an optimization of the adjustment for optimum in-coupling of excitation light by means of an in-coupling first diffractive grating structure towards measurement areas provided in direction of propagation of the in-coupled light is performed upon maximization of the excitation light out-coupled by an out-coupling second diffractive grating structure and measured by a detector.

46. The optical system according to claim 45, wherein a rotation of the optical component with several discrete facets for beam deflection, around an axis located inside or outside of said optical component, is performed for the optimization of the adjustment of the coupling angle.

47. The optical system according to claim 1, wherein the optical component with several discrete facets for beam deflection is connected with a rotary element with axis of rotation inside or outside of said optical component in such a way, that the offset of the beam on the sensor platform is less than 0.3 mm upon a rotation of said optical component around said axis of rotation by less than 5°.

48. The optical system according to claim 1, wherein the optical system comprises means for translation of the sensor platform in parallel or perpendicular to the grating lines for optimization of the coupling position.

49. The optical system according to claim 43, wherein an optimization of the adjustment for optimum in-coupling of excitation light by means of an in-coupling first diffractive grating structure towards measurement areas provided in the direction of propagation of the in-coupled light is performed upon maximization of one or more reference signals from one or more measurement areas on the sensor platform.

50. The optical system according to claim 49, wherein said reference signal is scattered light of the excitation wavelength.

51. The optical system according to claim 49, wherein said reference signal is luminescence light from measurement areas dedicated for purposes of referencing and/or of adjustment.

52. The optical system according to claim 1, wherein the irradiation of the excitation light to and detection of emission light from one or more measurement areas is performed sequentially for one or more measurement areas.

53. The optical system according to claim 52, wherein the sensor platform is moved between steps of sequential excitation and detection.

54. An analytical system, for the determination of one or more analytes in at least one sample on one or more measurement areas on a sensor platform of the optical system according to claim 1 by luminescence detection, whereby the analytical system comprises the optical system according to claim 1 and further comprises supply means for bringing the one or more samples into contact with the measurement areas on the sensor platform.

55. The analytical system according to claim 54, wherein said analytical system additionally comprises one or more sample compartments, which are at least in the area of the one or more measurement areas or of the measurement areas combined to segments open towards the sensor platform.

56. The analytical system according to claim 55, wherein the sample compartments have a volume of 0.1 nl-100 µl each.

57. The analytical system according to claim 55, wherein the sample compartments are closed, except for inlet and/or outlet openings for the supply or outlet of samples, at their side opposite to the first optically transparent layer, and wherein the supply or the outlet of the samples is performed in a closed flow-through system, wherein, in case of liquid supply to several measurement areas or segments with common inlet and outlet openings, these openings are addressed row by row or column by column.

58. The analytical system according to claim 55, further comprising parallel or crossed microchannels wherein the sample is applied by the parallel or crossed micro-channels upon exposure to pressure differences or electric or electromagnetic potentials.

59. The analytical system according to claim 55, wherein the sample compartments are provided with openings at the side facing away from the first optically transparent layer, for locally addressed supply or removal of the samples or of other reagents.

60. The analytical system according to claim 55, wherein the sample compartments are arranged in an array, comprising the sensor platform as the base plate and a body combined therewith in such a way, that an array of cavities is generated between the base plate and said body, for generation of an array of flow cells fluidically sealed against each other, and that at least one outlet of each flow cell leads to a reservoir fluidically connected with said flow cell and capable to receive liquid exiting from said flow cell.

61. The analytical system according to claim 60, wherein the reservoir for receiving liquid exiting from the flow cell is provided as a recess in the exterior wall of the body combined with the base plate.

62. The analytical system according to claim 54, wherein said analytical system comprises 2-2000 sample compartments.

63. The analytical system according to claim 55, wherein the geometrical arrangement in rows and/or columns of the inlets of the sample compartments does correspond to the geometrical arrangement of the wells of a standard microtiter plate.

64. The analytical system according to claim 60, wherein the arrangement of sample compartments with the sensor platform as the base plate and the body combined therewith does correspond to the footprint of a standard microtiter plate.

65. The analytical system according to claim 54, comprising 2 to 8 sample compartments in a column or 2 to 12 sample compartments in a row, wherein said sample compartments in a column or row are combined with a carrier ("meta-carrier") with the dimensions of standard microtiter plates in such a way, that the geometrical arrangement in rows and/or columns of the inlets of the flow cells does correspond to the geometrical arrangement of the wells of a standard microtiter plate.

66. The analytical system according to claim 60, wherein a removable bottom protection is provided below the sensor platform as the base plate of an arrangement of sample compartments, and wherein the upper side of the arrangement of sample compartments is closed with an additional covering top or a cover plate.

67. The analytical system according to claim 66, further comprising means for automatic or semi-automatic removal of the bottom protection before a measurement is started.

68. The analytical system according to claim 55, wherein the at least one first diffractive grating structure of a sensor platform is provided within each sample compartment.

69. The analytical system according to claim 55, wherein the sensor platform further comprises second diffractive grating structures for the out-coupling of excitation light, in addition to first diffractive grating structures for the in-coupling of excitation light, in order to out-couple again the light guided in the first optically transparent layer, after its passing through the region of the measurement areas in direction of propagation of the guided excitation light following an in-coupling first diffractive grating structure, and wherein the first diffractive grating structures are provided within the range of the sample compartments and said second diffractive grating structures for light out-coupling are always arranged outside of those sample compartments where the in-coupling is performed.

70. The analytical system according to claim 55, wherein the first diffractive grating structures extend over the range of several or of all sample compartments of the sensor platform.

71. The analytical system according to claim 55, wherein 5-5000 measurement areas are provided in one sample compartment.

72. The analytical system according to claim 60, further comprising a transport mechanism for an automated transport of an arrangement of sample compartments, said arrangement comprising a sensor platform as a base plate and a body combined therewith, from a location of the insertion of that arrangement to the location of luminescence excitation and detection.

73. The analytical system according to claim 54, wherein said analytical system additionally comprises a receiving device ("stacker") for receiving a plurality of arrangements of sample compartments.

74. The analytical system according to claim 73, wherein the loading of the "stacker" from the position of the insertion of the arrangement of sample compartments and the transport of said arrangement of sample compartments from there to the location of luminescence excitation and detection and then back to the original location is performed automatically.

75. The analytical system according to claim 54, wherein said analytical system comprises one or more temperature-controllable zones.

76. The analytical system according to claim 75, wherein the arrangement of sample compartments and/or the excitation light sources and/or the one or more opto-electronic detectors and/or the "stacker" can be temperature-controlled separately.

77. The analytical system according to claim 73, wherein the arrangement of sample compartments and/or the excitation light sources and/or the one or more opto-electronic detectors and/or the "stacker" are operated under a higher air pressure than ambient pressure.

78. The analytical system according to claim 54, wherein said analytical system additionally comprises one or more electronic control components for control of the status of one or more optical or electrical or mechanical components, which control components can generate an optical or acoustic or electronic alarm signal if necessary.

79. The analytical system according to claim 54, wherein said analytical system additionally comprises one or more electronic processors, connected to storage media and electronic connecting media, a keyboard for data or command input, a screen and a program code for automated operation.

80. The analytical system according to claim 54, wherein the operation of said analytical system and/or the measurement are performed automatically using pre-defined files for initialization.

81. The analytical system according to claim 54, wherein said analytical system is reset automatically to a pre-defined initial status and possibly generated measurement data are secured in a file, when an indicated error function has occurred.

82. The analytical system according to claim 54, wherein a file is generated automatically for each measurement, in which file are stored the code of the used sensor platform, the essential measurement parameters and the measurement data.

83. The analytical system according to claim 54, wherein local variations of the excitation light intensity on the sensor platform and/or of the detection sensitivity of the optical system for light signals from different positions on the sensor platform are corrected using means which comprise the recording of images for correction taken at the excitation wavelength and/or at one or more luminescence wavelengths, the calculation of theoretical distributions of the available excitation light intensity, theoretical calculations of the locally resolved efficiency of the optical imaging and detection system.

84. A method for the determination of one or more analytes by luminescence detection, upon using the analytical system according to claim 54, wherein one or more liquid samples to be analyzed for the one or more analytes are brought into contact with one or more measurement areas on the sensor platform, excitation light is directed towards the measurement areas, thus exciting compounds capable of luminescence in the sample or on the measurement areas to luminescence and the emitted luminescence is measured.

85. The method according to claim 84, wherein for generation of luminescence at least one luminescent dye or luminescent nanoparticle is used as a luminescence label, which can be excited and emits at a wavelength between 300 nm and 1100 nm.

86. The method according to claim 84 characterized in that it comprises means to extend the dynamic range for signal recording by at least a factor of 3.

87. The method according to claim 86, wherein the means for extending the dynamic range comprise the application of differently long exposure times, i.e., the duration of the irradiation of the excitation light and the integration time of the detector, which exposure times can be varied by at least a factor of 3.

88. The method according to claim 86, wherein the means for extending the dynamic range comprise a variation of the excitation light available on the sensor platform by at least a factor of 3, for example upon using discrete neutral density filters in the excitation beam path, optionally provided as a "continuously varying" filter with a continuous local gradient of the transmission, or upon variation of the intensity of the light sources or upon changing the adjustment of the sensor platform with respect to the excitation beam path.

89. The method according to claim 84, wherein the at least one luminescence label is bound to the analyte or, in a competitive assay, to an analyte analogue or, in a multi-step assay, to one of the binding partners of the immobilized biological or biochemical or synthetic recognition elements or to the biological or biochemical or synthetic recognition elements.

90. The method according to claim 84, wherein a second or more luminescence labels of similar or different excitation wavelength as the first luminescence label and similar or different emission wavelength are used.

91. The method according to claim 90, wherein charge or optical energy transfer from a first luminescent dye acting as a donor to a second luminescent dye acting as an acceptor is used for the detection of the analyte.

92. The method according to claim 84, wherein the one or more luminescences and/or determinations of light signals at the excitation wavelengths are performed polarization-selective.

93. The method according to claim 84, wherein the one or more luminescences are measured at a polarization that is different from the one of the excitation light.

94. The method according to claim 84 for the simultaneous or sequential, quantitative or qualitative determination of one or more analytes of the group comprising antibodies or antigens, receptors or ligands, chelators or "histidin-tag components", oligonucleotides, DNA or RNA strands, DNA or RNA analogues, enzymes, enzyme cofactors or inhibitors, lectins and carbohydrates.

95. The method according to claim 84, wherein the samples to be examined are naturally occurring body fluids, such as blood, serum, plasma, lymph or urine, or egg yolk or optically turbid liquids or tissue fluids or surface water or soil or plant extracts or bio- or process broths, or are taken from biological tissue fractions or from cell cultures or cell extracts.

96. A method comprising performing with the optical system according to claim 1, at least one or more quantitative or qualitative analyses for the determination of chemical, biochemical or biological analytes in screening methods in pharmaceutical research, combinatorial chemistry, clinical and pre-clinical development, real-time binding studies and the determination of kinetic parameters in affinity screening and in research, qualitative and quantitative analyte determinations, especially for DNA- and RNA analytics, generation of toxicity studies and the determination of gene and protein expression profiles, and the determination of antibodies, antigens, pathogens or bacteria in pharmaceutical product development and research, human and veterinary diagnostics, agrochemical product development and research, symptomatic and pre-symptomatic plant diagnostics, patient stratification in pharmaceutical product development and the therapeutic drug selection, the determination of pathogens, nocuous agents and germs, especially of salmonella, prions and bacteria, in food and environmental analytics.

97. The analytical system according to claim 55, wherein the sensor platform further comprises second diffractive grating structures for the out-coupling of excitation light, in addition to first diffractive grating structures for the in-coupling of excitation light, in order to out-couple again the light guided in the first optically transparent layer, after its passing through the region of the measurement areas in direction of propagation of the guided excitation light following an in-coupling first diffractive grating structure, and wherein first diffractive grating structures extend over the range of several or of all sample compartments.

98. The analytical system according to claim 55, wherein the sensor platform further comprises second diffractive grating structures for the out-coupling of excitation light, in addition to first diffractive grating structures for the in-coupling of excitation light, in order to out-couple again the light guided in the first optically transparent layer, after its passing through the region of the measurement areas in direction of propagation of the guided excitation light following an in-coupling first diffractive grating structure, and wherein the first diffractive grating structures and additional the second diffractive grating structures extend over the range of several or of all sample compartments.

99. A method for the determination of one or more analytes by luminescence detection, upon using the analytical system according to claim 55, wherein one or more liquid samples to be analyzed for the one or more analytes are brought into contact with one or more measurement areas on the sensor platform, excitation light is directed towards the measurement areas, thus exciting compounds capable of luminescence in the sample or on the measurement areas to luminescence and the emitted luminescence is measured.

100. A method comprising performing with an analytical system according to claim 54 at least one or more quantitative or qualitative analyses for the determination of chemical, biochemical or biological analytes in screening methods in pharmaceutical research, combinatorial chemistry, clinical and pre-clinical development, real-time binding studies and the determination of kinetic parameters in affinity screening and in research, qualitative and quantitative analyte determinations, especially for DNA- and RNA analytics, generation of toxicity studies and the determination of gene and protein expression profiles, and the determination of antibodies, antigens, pathogens or bacteria in pharmaceutical product development and research, human and veterinary diagnostics, agrochemical product development and research, symptomatic and pre-symptomatic plant diagnostics, patient stratification in pharmaceutical product development and the therapeutic drug selection, the determination of pathogens, nocuous agents and germs, especially of salmonella, prions and bacteria, in food and environmental analytics.

101. The optical system according to claim 16, wherein a thin metal layer is deposited between the first optically transparent layer and the adhesion-promoting layer with immobilized biological or biochemical or synthetic recognition elements thereon, wherein the thickness of the metal layer and of the adhesion-promoting layer is selected in such a way that surface plasmon can be excited at the excitation and/or luminescence wavelength.

102. The optical system according to claim 1, wherein the first diffractive grating structure is a relief grating structure.

103. The optical system according to claim 30, wherein the second diffractive grating structure is a relief grating structure.

* * * * *